(12) United States Patent
Mäkiranta et al.

(10) Patent No.: US 8,026,716 B2
(45) Date of Patent: Sep. 27, 2011

(54) DEVICE FOR MEASURING MAGNETIC PARTICLES AND CORRESPONDING METHOD

(75) Inventors: Jarkko Mäkiranta, Siuro (FI); Jukka Lekkala, Tampere (FI)

(73) Assignee: Magnasense Technologies Oy, Jyvaskyla (FI)

( * ) Notice: Subject to any disclaimer, the term of this patent is extended or adjusted under 35 U.S.C. 154(b) by 309 days.

(21) Appl. No.: 12/226,112

(22) PCT Filed: Apr. 20, 2007

(86) PCT No.: PCT/FI2007/050211
§ 371 (c)(1),
(2), (4) Date: Oct. 7, 2008

(87) PCT Pub. No.: WO2007/122293
PCT Pub. Date: Nov. 1, 2007

(65) Prior Publication Data
US 2009/0243603 A1   Oct. 1, 2009

(30) Foreign Application Priority Data

Apr. 21, 2006 (FI) ..................................... 20065257
Jul. 27, 2006 (FI) ..................................... 20065502

(51) Int. Cl.
*G01B 7/30* (2006.01)
(52) U.S. Cl. ................................................. 324/207.25
(58) Field of Classification Search .................. None
See application file for complete search history.

(56) References Cited

U.S. PATENT DOCUMENTS

| 5,001,424 A | * | 3/1991 | Kellett et al. ............. 324/204 |
| 2005/0093535 A1 | * | 5/2005 | Kriz ............................. 324/201 |

FOREIGN PATENT DOCUMENTS

| EP | 0773440 | 5/1997 |
| GB | 2186978 | 8/1987 |
| WO | 03076931 | 9/2003 |
| WO | 2005111614 | 11/2005 |

OTHER PUBLICATIONS

Jarkko J. Makiranta, et al. Modeling and simulation of magnetic nano particle sensor. Proceedings of the 2005 IEEE-Engeneering in Medicine and Biology 27th Annual Conference Shanghai, China, Sep. 1-4, 2005.

Yin Yong-hui et al., *Design of the inductive transducer of wear particle monitoring*, Journal of Transducer Technology, vol. 22, 2003, No. 7.

* cited by examiner

Primary Examiner — Jermele M Hollington
(74) Attorney, Agent, or Firm — Fildes & Outland, P.C.

(57) ABSTRACT

The invention concerns a device for the qualitative or quantitative measurement of a magnetically labelled analyte. The device includes a coil arrangement for measuring the analyte from a sample absorbed in a test base. The coil arrangement includes at least one measuring coil and a reference coil arranged in connection with it. From the signal of the coil arrangement a change in inductance correlating to the content of the magnetically labelled analyte is arranged to be detected. The change in inductance is arranged to be detected from a change ($\Delta A$, $\Delta \phi$) in amplitude and/or phase appearing in the output signal of the coil arrangement, which is arranged to be measured at the frequency of the input signal. In addition, the invention also relates to a corresponding method.

18 Claims, 8 Drawing Sheets

DEVICE FOR MEASURING MAGNETIC PARTICLES AND CORRESPONDING METHOD

BACKGROUND OF THE INVENTION

The present invention concerns a device for the qualitative or quantitative measurement of a magnetically labelled analyte, which device includes a coil arrangement, formed of at least one measuring coil and a reference coil arranged in connection with it, for measuring the analyte from a sample absorbed in a test base, and from the signal of which coil arrangement a change in inductance correlating to the content of the magnetically labelled analyte is arranged to be detected. In addition, the invention also relates to a corresponding method.

Numerous methods and apparatuses for measuring magnetic particles, for example, in analytic tests, are known from the prior art. For example, Finnish patent number 113297 discloses an idea concerning the use of a so-called astatic coil arrangement for measuring an analyte from a sample absorbed in a test base. In it, the coil arrangement is used to detect a change in inductance correlating to the content of a magnetically labelled analyte.

The application of traditional coil technology to such an arrangement, however, is associated with significant problems relating, for example, to the sensitivity of the apparatus. Some examples of these are capacitive parasitic current in the coil loops. Another problem can be mentioned the asymmetry of the coils, which is caused by, for example, the manual winding of the coils.

The magnetism of magnetic particles and thus the change in inductance they create in a coil system is very insignificant compared, for example, to the error signals caused by the environment or the test base itself. Thus the measurement results obtained using the apparatus leave much to be desired.

In addition, due to the test bases according to the prior art, the reactions of the analyte on the test base take place on a very small scale, due, for example, to expensiveness of the reagents. Therefore the positioning of the test base relative to the device, for example, creates a challenging problem while wrong positioning can distort the test results. In addition, the test base places special demands particularly on wrapped coil constructions.

The solutions disclosed in PCT publications WO-2005111614 and WO-2005111615 also make known the application of coil devices in analytic rapid tests. They are based on detecting a change of inductance from a change in resonance frequency. When measuring the change in resonance frequency, the resonance peak of the LC circuit changes to a different frequency when the inductance of a coil or the capacitance of a capacitor changes. However, the low inductance of the coil creates a problem. Parasitic phenomena of all kinds can easily connect to a coil with a low inductance, and thus they can also be distinguished from the signal measured in the frequency form.

PCT publication WO 03/076931 A1 discloses yet another manner of measurement known from the prior art. It too is based on detecting changes in frequency.

Various so-called SQUID-type methods are also known. However, their operating principle demands operation at very low temperatures, at even close to absolute zero. This makes the apparatus complicated, for example, in POCT (point of care testing) applications.

SUMMARY OF THE INVENTION

The present invention is intended to create an improved device and corresponding method for measuring a magnetically labelled analyte qualitatively or quantitatively, by means of which substantially more accurate measurement information can be created than when using known apparatuses, based, for example, on coil arrangements operating at room temperature. The characteristic features of the device according to the invention are stated in the accompanying claim 1 while the characteristic features of the method corresponding to it are stated in claim 15.

In the device according to the invention, a change in inductance is arranged to be detected from a change in amplitude and/or phase appearing in the output signal of the coil arrangement, which is arranged to be measured at the frequency of the input signal.

According to one embodiment, in order to increase the inductive reactance to be greater than the resistance, the measuring frequency used in the device is arranged to be $10^5$-$10^9$ Hz, preferably $10^6$-$10^8$ Hz. The use of such very high measuring frequencies will surprisingly improve the accuracy of the measurement results obtained using the device.

According to one more highly developed embodiment, the device can additionally include a coil arrangement compensating for error signals, which can be formed in several different ways. It can be used to compensate, for example, for error signals caused by the environment and/or magnetic particles that are unspecifically bound to the test base. The reference coil can, for its part, also be used for this compensation purpose. It can be used to compensate for, among other things, error signals caused by the test base. Of course, it should be noted that, in the device according to the invention, the reference coil has other functions too, so that the compensation function referred to in this connection does not in any way exclude other functions. The compensating construction can, according to one embodiment, be implemented, for example, as a differential coil system. One example of this can be an impedance bridge. In that case, the measuring coil and the reference coil are in connection with the compensating construction.

By means of the device according to the invention, very accurate measurement results can be obtained, even in the case of very weak magnetic analytes. The high measuring frequencies applied in the measurement, and the differential coil construction mean that the device is eminently suitable for use at even room temperature, in terms of its temperature conditions. Compared to the frequency measurements of the prior art, the device and method according to the invention are less sensitive to parasitic phenomena, as they are not distinguished as easily from the measured output signal, which the phase difference and/or amplitude is measured at the frequency of the input signal.

According to one embodiment, the device can also be made very end-user-friendly. If the test base is integrated in interaction with the coil arrangement, it will not need to be separately set to a connection with the coil means. It will then be sufficient for the sample to be placed on the base and the measurement to be performed. As a device embodiment, this can be considered particularly precisely in coils in the microsize scale and, for example, in Point-of-Care Testing i.e. POCT applications.

Other characteristic features of the device and method according to the invention are stated in the accompanying Claim while additional advantages achieved are itemized in the description portion.

BRIEF DESCRIPTION OF THE DRAWINGS

In the following, the invention, which is not restricted to the embodiments described in the following, is examined in greater detail with reference to the accompanying drawings, in which.

DETAILED DESCRIPTION

By means of the devices 10 according to the invention and of a measuring method based on them, it is possible to detect the amount of magnetic particles from a test base 11. The measurement is based on using a coil arrangement 13, 18-20, in the operation of which the presence of magnetic particles will cause a detectable divergence.

Figure 1:
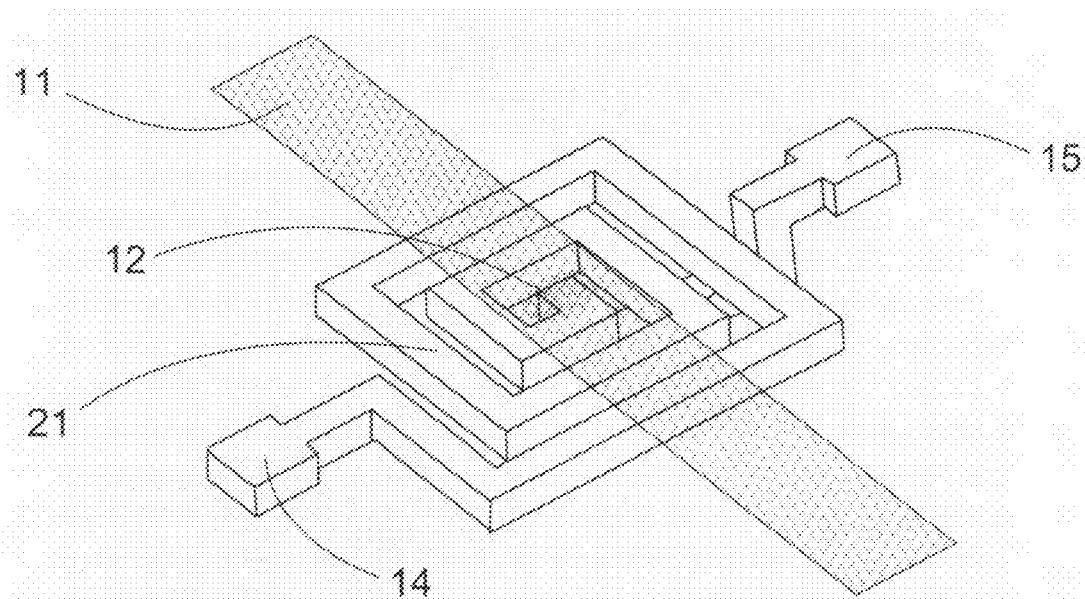
FIGS. 1-3 show some possible examples of the coil constructions to be used in the device according to the invention.
Figure 2:
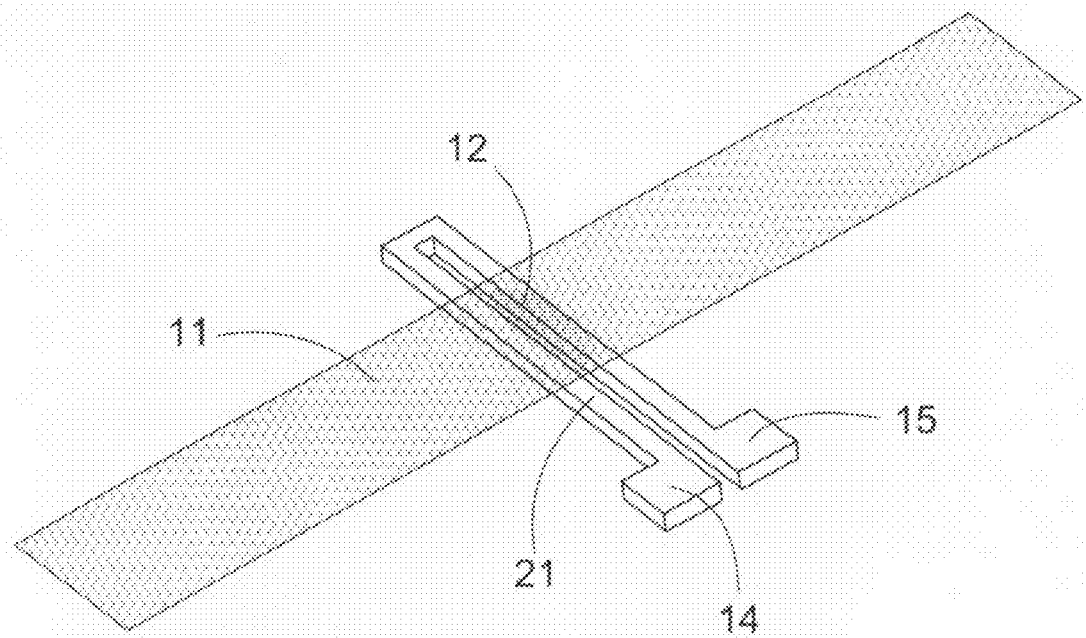
Figure 3:
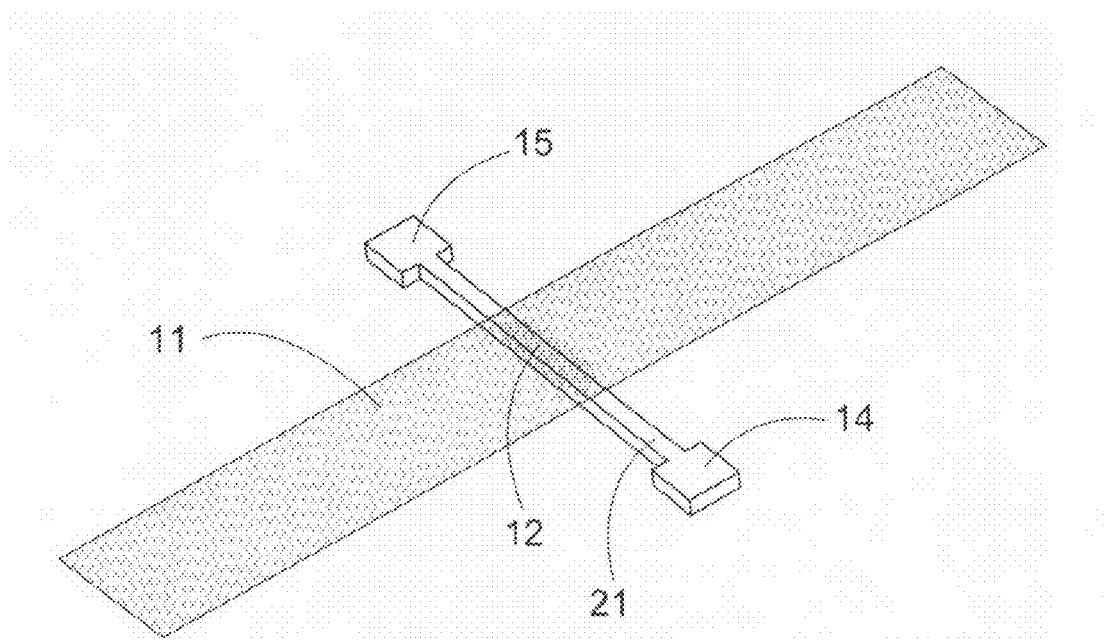

FIGS. 1-3 show some simplified examples of the coils 21 suitable for use in devices 10 according to the invention, for the qualitative or quantitative measurement of a magnetically labelled analyte 12.

FIG. 1 shows a first example of a coil 21, which can be applied in the device 10. In this case, the coil construction forms a planar rectangular spiral, the number of turns of which is now two. The elongated test base 11 can be positioned quite freely, but in any event asymmetrically, relative to the coil 21, more general, the coil arrangement of the device. In this case, the test base 11 runs across the coil 21, its longitudinal direction being at right angles to the direction defined by the contact terminals 14, 15, from which contact terminals 14, 15 the coil loop 21 can be connected. An example of the inductance interval of such a coil 21 can be generally 1 pH-1 mH, more specifically 1 nH-1000 nH and the resistance interval generally 1-100 Ω, more specifically 10 mΩ-10 Ω (depending on the measuring frequency used). In general, it can be stated that the main effective factor of the resistance and inductance values is the dimensions of the coil. In this case, the reading values given are fitted to the coil dimensions referred to later.

FIG. 2 shows a second example of the coil 21 used in the device 10. As the embodiment shows, the construction of the coil 21 can be very simple indeed. Now the coil is formed of only a single conductor loop, being thus a simplified version of the coil construction shown in FIG. 1. The conductor loop forms a single-winding, planar coil 21, with which an interactive connection can be arranged from the test base 11 with the magnetic particles 12. In this case too, to the coil loop 21 is connected from contact terminals 14 and 15, which are now on the same side. One example of the inductance interval of the coil loop 21 for such a coil construction can be 1 nH-20 nH, while the resistance interval can be 1 mΩ-100 mΩ.

FIG. 3 shows a third example of the construction of a single coil 21. In this case, the coil 21 is formed of an even simpler construction than in the two cases described above. The example shows that the coil 21 can even be formed of a straight conductor structure, a conductor beam, which is drawn across the test base 11. Despite the simplicity of the construction, this construction too is understood to be still undisputably a coil, as the conductor beam 21 now forms the coil component in the electrical circuit when it is connected to the electronics. Again, to the conductor 21 can be connected from the contact terminals 14, 15. One example, of the inductance interval with such a construction can be 100 pH-3 nH and the resistance interval 0.1 mΩ-10 mΩ.

Figure 4:
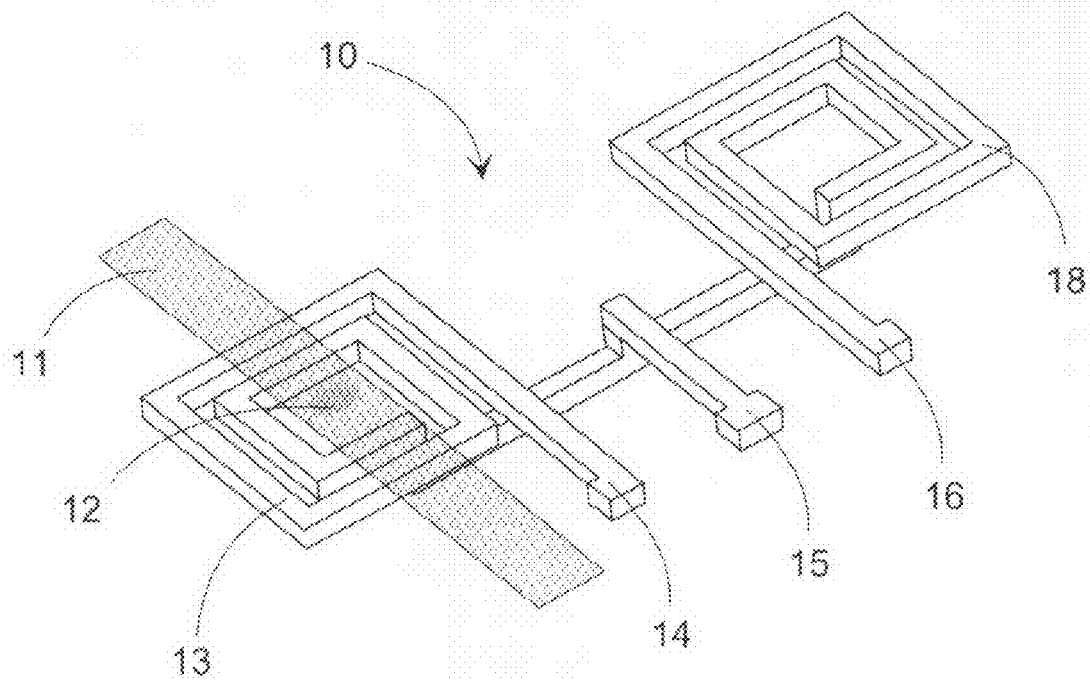
FIG. 4 shows a first embodiment of the device according to the invention, in which a differential coil pair is applied.
Figure 5:
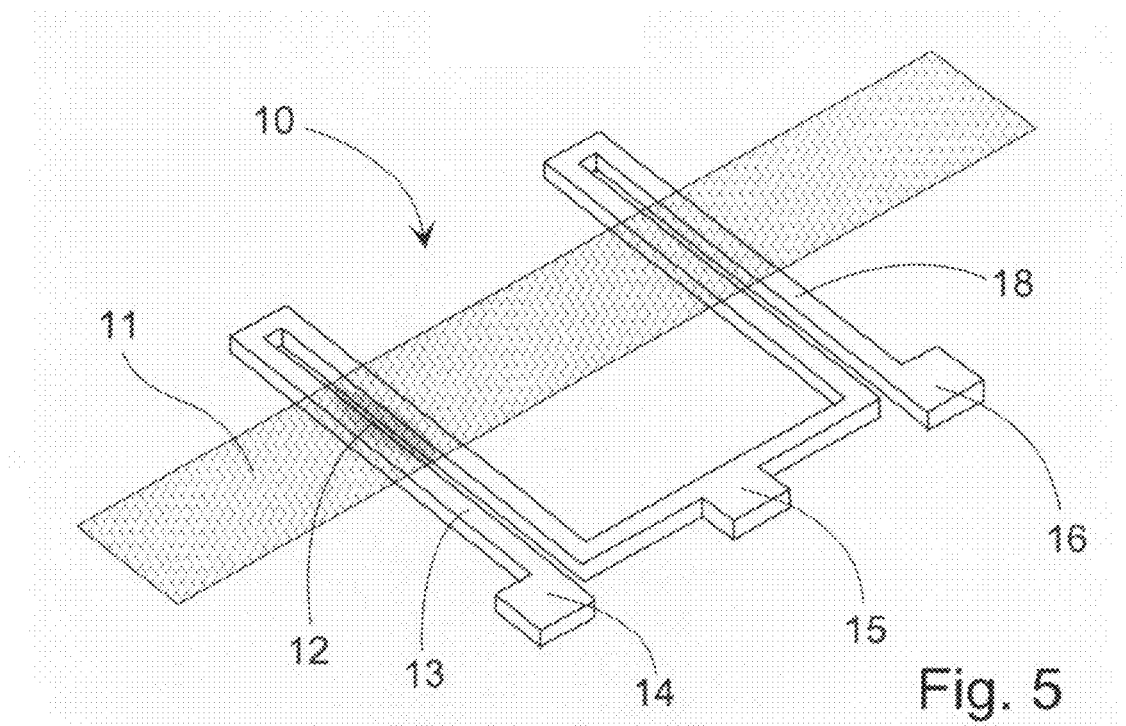
FIG. 5 shows a second embodiment of the device according to the invention, in which a differential loop coil pair is applied.
Figure 6:
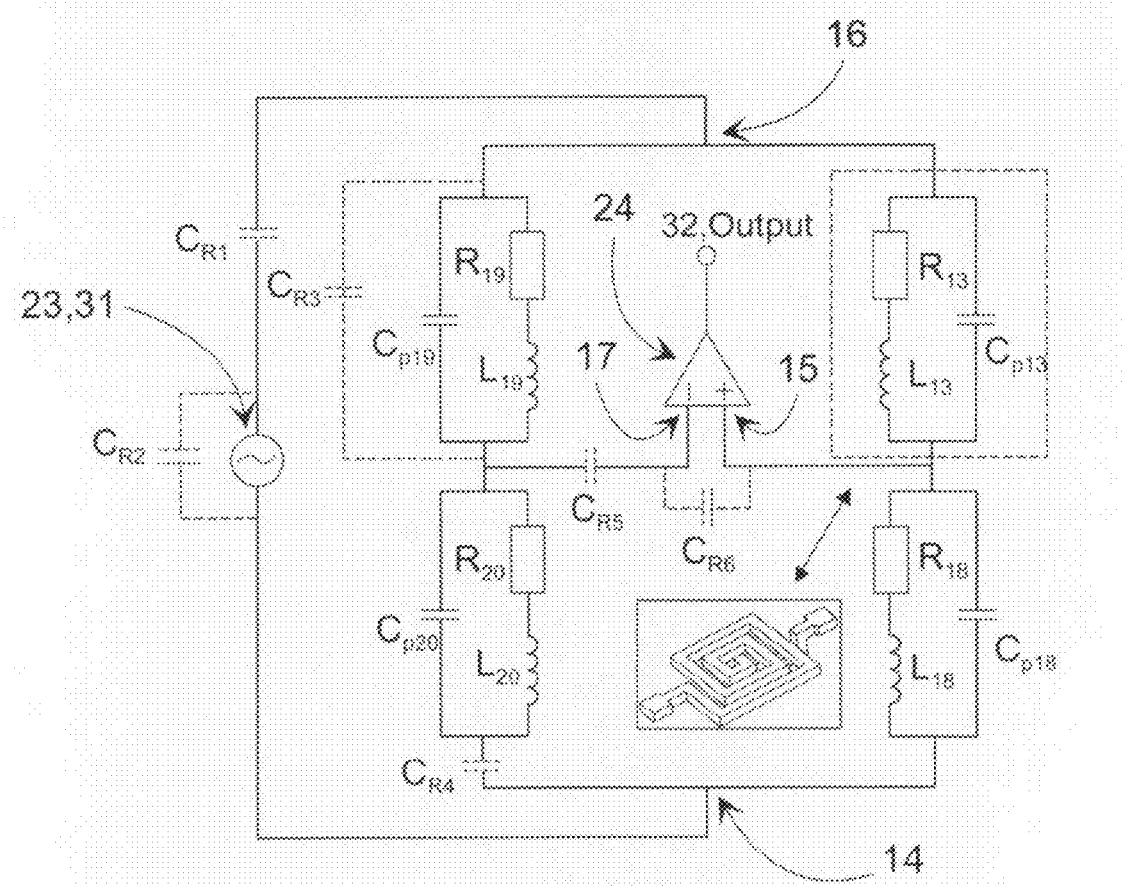
FIG. 6 shows an embodiment, modelled with circuit components, of the device according to the invention, in which the bridge measuring principle is applied, FIG. 7 show an example of measuring arrangement applying the bridge measuring principle of FIG. 6.

FIGS. 4 and 5 shows some embodiments of devices 10 according to the invention, in which the coil constructions shown in FIGS. 1-3 can be applied. In the device 10 according to the invention, the coil arrangement, by means of which an analyte 12 is measured from a sample absorbed on a test base 11, includes in its basic form at least two coils 13, 18 formed of conductor structures, the conductor structures of which can be, for example, planar and connected to each other galvanically. It should be noted that FIGS. 1-10 do not show, for reasons of simplicity, the insulations possibly required on the circuit board 22, or the equipment relating to the measuring electronics, which the implementation of the device 10 in practice requires/may demand. FIG. 6 shows such a totality with all its details.

The device 10 shown in FIG. 4 includes two planar square-spiral shaped coils 13, 18, both of which are next to each other on the same plane and connected in series. The coil 13 is used for the actual measurement and close to it is a coil 18 as a reference for the measuring coil 13, which in this case forms, for its part, a compensating construction. The reference coil 18 fitted in connection with the measuring coil 13 can be, for example, an identical copy of the measuring coil 13, or its mirror image, being aligned symmetrically relative to the measuring coil 13. The use of the identical copy or mirror-image property improves the interference immunity of the coil arrangement. The distance between the coils 13, 18 is arranged to be such that they are sufficiently close to each other in terms of measurement, but on the other hand, however, in such a way that the magnetic fields of the coils 13, 18 will not significantly interact with each other in terms of the measurement. The coils 13, 18 are wound in the same direction.

It should be noted, that the measuring coil 13 and the reference coil form a single compact totality, so that the coil arrangement formed by them and the test base 11 set in connection with them interact mutually and the output is a single measurement signal 32, from the change in amplitude and/or phase ΔA, Δϕ (delta A, delta phi) measured from which at the frequency of the input signal 31 the necessary conclusions concerning the analyte being examined can be drawn. This simplifies the construction and operation of the sensor 10.

The reference coil arrangement, which in this case includes a single reference coil 18, has in the device according to the invention several different implications, which do not exclude each other. A first function of the reference coil is to compensate the self-inductance, resistance, temperature dependence of the resistance, and capacitance of the measuring coil 13. In general, it is possible to speak of the compensation of the electrical parameters caused by the coil 13 itself and of the changes not caused by those magnetic particles. When the self-inductances of the coils 13, 18 are the same, the difference proportional to the amount of particles, owing to which the measurement can be said to be differential, will appear in the output of the measuring coil 13. In addition, the reference coil 18 can also be used for its part to compensate the errors caused by the test base 11 and/or the environment, which also for its part relates to the differential nature of the arrangement. For example, the unspecifically bound particles in the test base 11, the possible capacitive connection between the turns of the coil and the material of the test base 11, and the capacitive connection between the medium (sample solution, or similar) transporting the samples and particles and turns of the coil, can be classified as errors caused by the test base 11. Sources of error caused by the environment are, for example, the change in resistance caused by temperature variations, error signals induced from the input electronics 23, the Earth's magnetic field, and other disturbances.

The particles 12 on the test base 11 are detected using the measuring coil 13. The measurement can be performed as a so-called intermediate output measurement, from the contacts 15 between the coils 13, 18. The alternating current signal fed from the contacts 14, 16 over the coils 13, 18 sums as zero in the intermediate output 15, if the test base 11 is particle free. The magnetic field of the measuring coil 13 belonging to the coil arrangement is used to magnetize the particles to be detected, which are made to interact with at least the measuring coil 13 of the device 10. The magnetized particles reinforce the measuring coil's 13 own magnetic field, so that the measuring coil 13 sees the change as a change in inductance. As a result of the strengthening of the magnetic field of the measuring coil 13, a voltage, which is compared to the ground of the input signal, proportional to the number of particles, appears in the intermediate output 15. In this connection, it is indeed possible to speak of a differential connection, i.e. the output is the difference between two signals.

Thus, the coil arrangement 13, 18-20 of the device 10 can be used to detect a change in inductance corresponding to the content of a magnetically labelled analyte 12, which in the device 10 and method according to the invention is measured from a change in amplitude and/or phase $\Delta A$, $\Delta \phi$ appearing in the output signal 32 of the coil arrangement 13, 18, which is measured at the frequency of the input signal 31. According to one embodiment, this can be measured from the change in amplitude and/or phase $\Delta A$, $\Delta \phi$ of the intermediate output 15 of the measuring coil 13 and the reference coil 18. This manner of measurement achieved a particular advantage that will be returned to later in this description. The change in inductance is proportional to the number and location of the particles, which are the intended measurement results and from which conclusions can be drawn concerning the results of the test. In the case of the device according to the invention it is indeed possible to speak of an impedance/inductance sensor, in which the properties of the coil conductor are measured.

In FIG. 4, the test base 11 is placed on top of only the measuring coil 13. Alternatively, the test base 11 could be arranged over both coil branches 13, 18, as shown by the embodiment in FIG. 5. There is an electrical connection from the contact terminals 14-16 to the measuring arrangement formed by the coils 13, 18.

FIG. 5 shows a second embodiment of a differential sensor-loop pair, which is now formed of two single-winding planar coil loops 13, 18 parallel to each other. The construction is slightly simpler than the embodiment shown in FIG. 4 and thus more affordable to manufacture. In this embodiment, the test base 11 with the magnetic particles 12 is placed transversely on top of both coils 13, 18. Having the test base 11 on top of both coils 13, 18 improves, among other things, the elimination of measurement errors caused by the test base 11. There is a connection to the measuring system from the contact terminals 14-16, of which 15 is again a common intermediate output for both coils 13, 18. It should be noted that each coil 13, 18 can also have its own contact terminal 14-16, independent of the embodiment.

In both embodiments, the measuring coil 13 and the reference coil 18 forming the compensating structure for that thus now form a differential coil arrangement. The reference coil 18 arranged in connection with the measuring coil 13 can be used to measure differentially the amplitude A and/or the phase $\phi$ of the output signal 32 correlating to the change in inductance of the measuring coil 13. This minimizes the ambient interferences and particularly the error signal caused by excess unspecifically located magnetic particles.

The device 10 can include even several compensating structures for error signals. The number of structures and their connection to the measuring coil 13 depends on the measuring variations in each case.

FIG. 6 shows an embodiment of the device 10 modelled with circuit components, in which the bridge measurement principle is applied using four coils 13, 18-20. The compensating additional structures 19, 20 or structure and their placing (for example, symmetry, overlapping) can be used in this case primarily to eliminate error signals caused by the environment. These can be caused, for example, by electromagnetic machines and devices and also by the Earth's magnetic field. In addition, bridge measurement permits 'floating measurement', in which the signal is not compared to the ground potential, which might otherwise cause errors.

In this case, the compensating structure includes not only the reference coil 18, but at least two additional coils 19, 20. In this case, the measuring coil 13, reference coil 18, and the compensating structure 19, 20 are arranged in an impedance bridge relative to each other. In addition, the coils 13, 18-20 are also arranged symmetrically relative to each other. In that case, the coils 13, 18-20 can be, for example, identical copies or mirror images of the measuring coil 13, which properties are used to improve the interference tolerance of the arrangement. The measuring coil 13, reference coil 18, and compensating structure 19, 20 can thus be, for example, the same magnitude of, their inductance, resistance, and/or capacitance. Thus at least some of their electrical parameters can be of the same magnitude. The application of identical coils allows the sensitivity of the bridge measurement to be considerably increased, as all the impedances will be mainly of the same magnitude.

The impedance bridge is thus formed of the measuring coil 13, its reference coil 18, and their compensating coils 19, 20. The test base 11 can be arranged, for example, in the manner shown in FIGS. 8-10, over at least the measuring coil 13 and in this case also the reference coil 18. The rest of the coils 19, 20 are for compensation. In FIG. 6, the coils 13, 18-20 are shown depicting their general equivalent circuits (coil L, series resistor R, and parallel capacitor $C_p$). The signal source is marked with the reference number 23.

FIG. 6 also includes some possible ways ($C_{R1}$-$C_{R6}$) of placing the resonance capacitor. One example of a way to arrange the resonance capacitors can be such that the capacitors are on the input side of the circuit to be connected in series and those on the measuring side to be connected in parallel.

The capacitors can also be manufactured together with the coils 13, 18-20 on a common base 22. The advantage of this is that it easily achieves a first amplification stage increasing the signal.

In the bridge connection, the signal 32 is measured between two separate pairs of coils. The signal 32 obtained from the intermediate output 15 of the measuring coil pair 13, 18 is compared to the intermediate output 17 of the corresponding compensating coil pair 19, 20 without particles, so that it is also possible to speak of a differential measurement. In the same way it is also possible to speak of a 'floating' measurement, because the actual output, i.e. measuring signal 32 is compared with the ground potential, which is not in galvanic contact, for example, with the ground potential of the input device 23.

Figure 8:
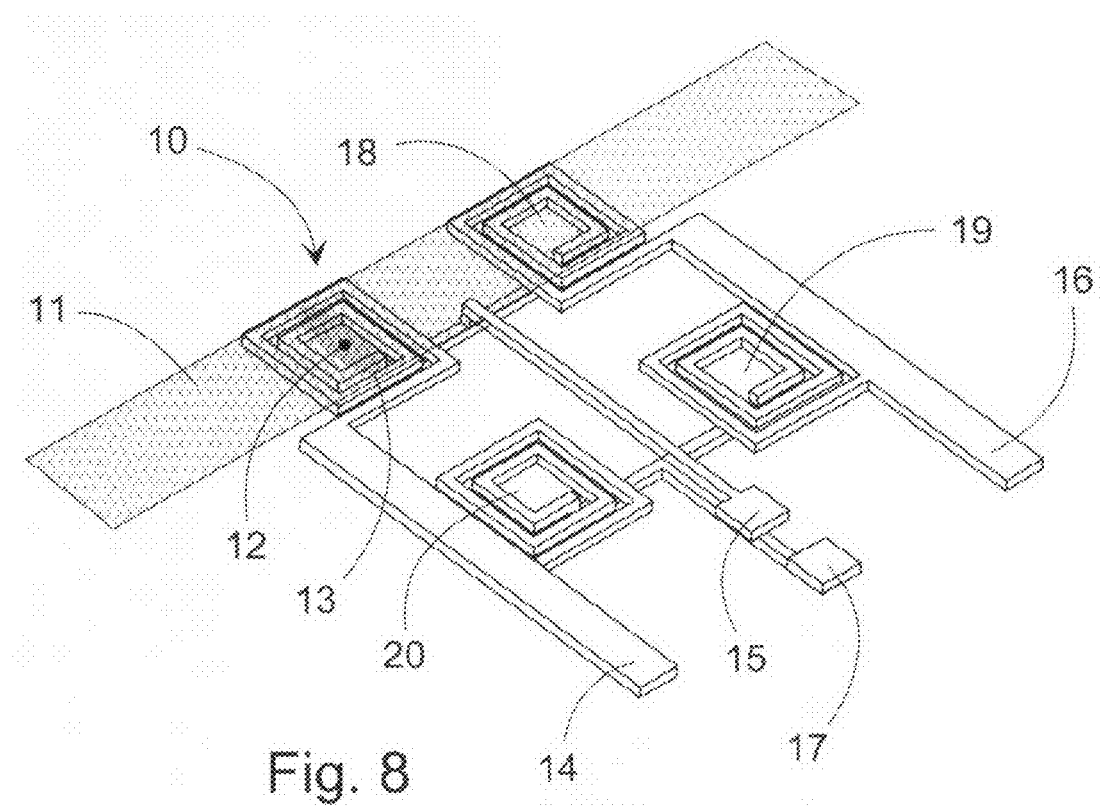
FIG. 8 shows a third embodiment of the device according to the invention, in which bridge measuring with the coils being on the same plane, is applied.
Figure 9:
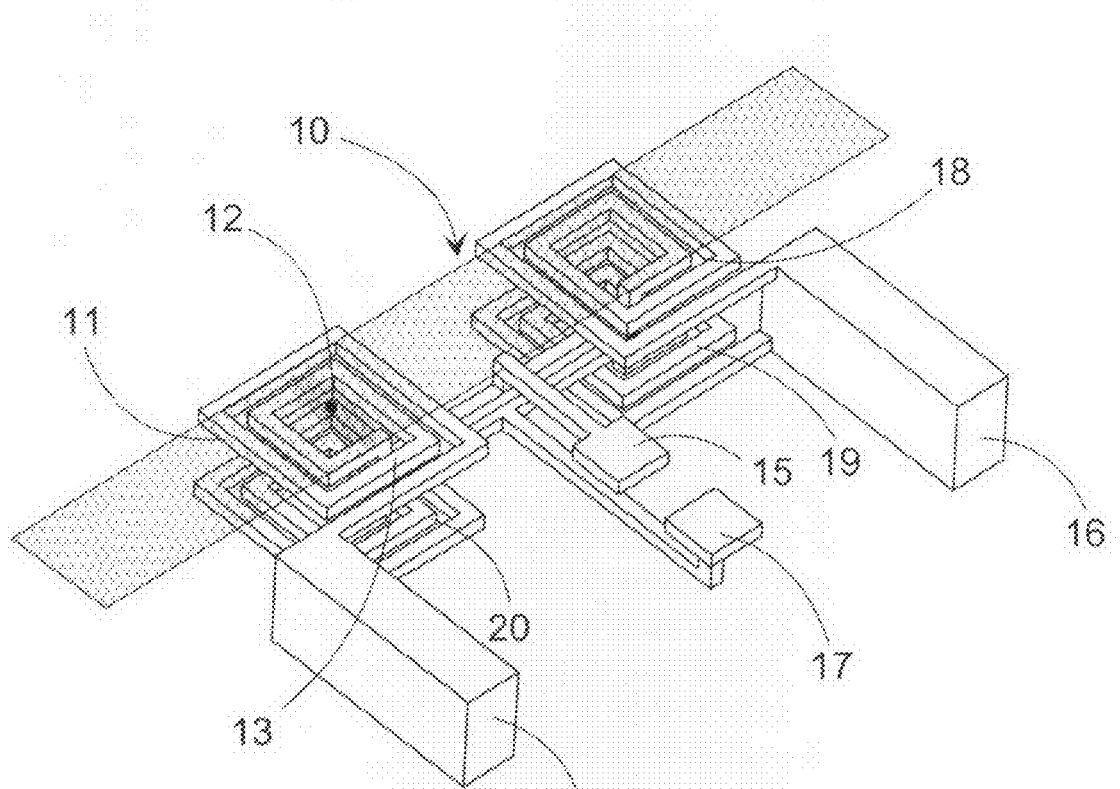
FIG. 9 shows an embodiment of the device according to the invention, in which bridge measuring is applied, and in which at least some of the coils are on different planes.
Figure 10:
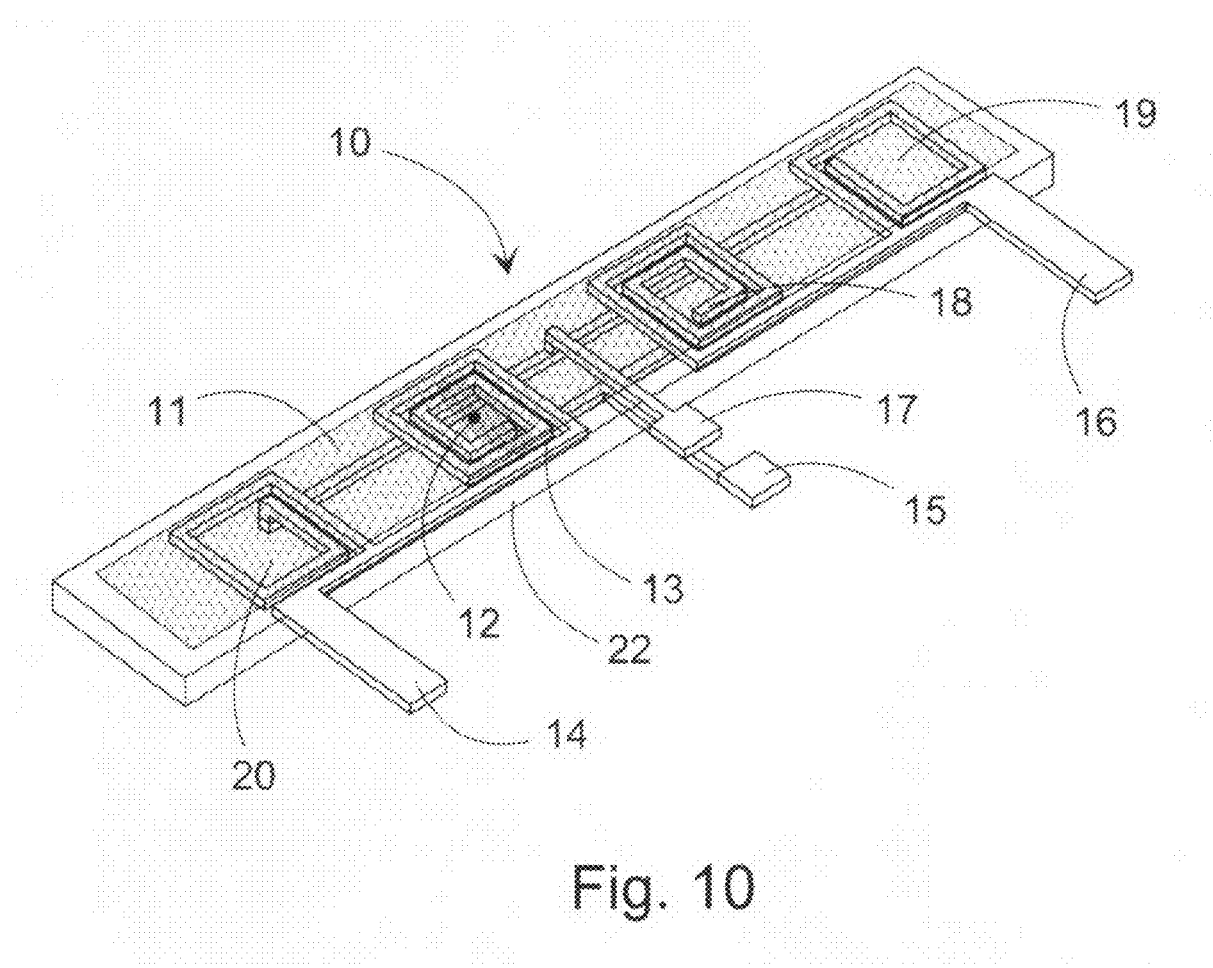
FIG. 10 shows an embodiment of the device according to the invention, in which bridge measuring is applied, and in which the coils are in a row on the same plane.

FIGS. 8-10 show some possible ways of placing coils 13, 18-20 for a four-coil bridge measurement. FIG. 8 shows an embodiment, in which all the coils 13, 18-20 are on the same level, being in a matrix-like formation. In it the measuring coil 13 and the reference coil 18 are aligned symmetrically relative to the measuring-signal conductors 15 and 17. The compensation coils 19, 20 are next to each other like squares on the same level. In addition, they are symmetrical relative to at least one axis with the measuring signal conductors 15, 17 and the first coil pair 13, 18. Because the current leaving the measuring-signal conductors 15, 17 is considerably smaller than the current brought to the input-signal conductors 14, 16, a symmetrical arrangement of this kind achieves a significant additional advantage, for example, in the compensation of interferences. The symmetrical continuity can extend to the area of influence of the coils 13, 18-20. The area of influence of the coils 13, 18-20 can be said to end when the ambient interference becomes dominant.

The test base 11 with the magnetic particles 12 is located transversely on top of both coils 13, 18. The input-signal conductors 14, 16 are at the sides of the circuit card and the measuring-signal conductors 15, 17 in the middle on two levels. The output signal 32 is measured between the two measuring-signal conductors 15, 17 ('Output' in FIG. 6).

FIG. 9 shows another embodiment of the bridge measurement. In it, the coil pairs 13, 18, 19, 20 are on top of each other. In general, it is possible to speak of a layered arrangement, in which at least some of the coils are on a different level to the others. The coils 13, 18 on the same level can then be parallel to each other, such as, for example, symmetrically in pairs. If there is precious little unspecific bonding, there coils 13, 18-20 can be singly, as will be described later in greater detail.

The measuring coil 13 and the reference coil 18 are once again aligned symmetrically relative to the measuring-signal conductors 15, 17. The input-signal conductors 14 and 16 come at the sides. Unlike the embodiment shown in FIG. 8, the compensation coils 19, 20 are now under the measuring coil 13 and the reference coil 18. In this embodiment, the test base 11 with the magnetic particles 12 is located transversely on top of both 'coil stacks'. In this case, the stacked geometry of the coils 13, 18-20 minimizes interferences better than in the embodiment shown in FIG. 8. In addition, this embodiment permits a better placing of the coils on the test base 11. This is an advantage, especially when using a lateral-flow test.

FIG. 10 shows a third embodiment of bridge measurement, in which the coils 13, 18-20 are again on the same level, but in this base in a row formation. Again, the measuring coil 13 and the reference coil 18 are aligned symmetrically relative to the measuring-signal conductors 15, 17. Also in this case, the input-signal conductors 14, 16 come from the sides. The compensation coils 19, 20 are now at the ends of the coil array on either side of the measuring and reference coils 13, 18. The test base 11 with the magnetic particles 12 is again located transversely on top of all the coils 13, 18-20. One advantage of this construction is a better alignment relative to the test base 11.

According to yet another bridge-measurement embodiment, the coils 13, 18-20 can also be concentrically on a post. In this case, reference can be made to FIG. 9. The signal conductors of the measuring and reference coils 13, 18 can, differing from FIG. 9, also be run in such a way that if necessary insulating material can be removed from around the coils, for example, by milling. In this way, the measuring and reference coils 13, 18 can be made clearly higher that their surroundings, such as, for example, other conductors. For example, the conductor 17 of FIG. 9 could be made to run behind and under the conductor 15. The advantage of the construction is a better alignment on some test bases.

According to one embodiment, the test base 11 can also be integrated in the sensor structure 13, 18-20 on a separate disposable base 22 (FIG. 10). In that case, at least the measuring coil 13 will be integrate in the immediate vicinity of the test base 11, being attached to or at least very close to it (distance<$\frac{1}{10}$ of the diameter of the coil 13). In any event, independent of the arrangement, it is possible to speak of an interactive connection between the test base 11 and the coil arrangement, at the very least the measuring coil 13. Corresponding ways of arranging the connection of the test base 11 and the coils 13, 18 are also possible in a such device, in connection with which the test base 11 can be brought in a detachable manner. On the same base 22, it is also possible to integrate some or all of the coils (reference coil 18, compensation coils 19, 20) and/or at least part or even all of the measuring electronics. The integrated disposable base 22 can be connected to the rest of the electronics, for example, galvanically, capacitively, or inductively.

As the embodiments described above show, the test base 11 can be located not only parallel to the coil plane (XY plane), but also perpendicularly through the coil plane (Z axis). The test area can also be transverse to the measuring coil 13 (in the XY plane).

Irrespective of the degree of integration, the coil arrangement according to the invention can be manufactured typically on an insulator or a semiconductor. Such an insulator can be, for example, glass (quartz), plastic (FR4), or a semi-conducting oxide ($SiO_2$). The insulator material used depends on the manufacturing technique. The measuring coil 13, the reference coil 18, and the possible compensating coils/structures 19, 20 can be made from an electrically conductive metal, such as, for example, copper, aluminium, gold, or silver, but also from other electrical conductors, such as, for example, electrically conductive polymers, or a doped semiconductor. To manufacture the structures, it is possible to use, for example, micro-machining methods, such as, for example, photolithography, wet or dry etching, doping, metallization, printing electronics, and/or thick-membrane techniques. The structures can also be made using mechanical machining methods, such as, for example, by milling.

According to one embodiment, in order to increase the inductive reactance of the coil arrangement, such as, for example, of the measuring coil 13, the measuring frequency of the device 10 can be adapted to be higher than the known measuring frequencies of the prior art. One example of such a measuring frequency can be $10^5$-$10^9$ Hz and more particularly $10^6$-$10^8$ Hz. At small dimensions $10^{-7}$-$10^{-1}$ m, more particularly $10^{-5}$-$10^{-3}$ m, of the coils 13 of the device 10, and at high measuring frequencies $10^5$-$10^9$ Hz and more particularly $10^6$-$10^8$ Hz, a greater sensitivity than that of earlier inductance change measuring devices and methods will be achieved. In the method according to the invention, measurement is performed using the same frequency as the input signal 31 fed to the coil arrangement 10. Though in some cases or in some measuring arrangements the frequency might change, this will not be detected, because it is not measured in the case of the invention. Instead of the frequency change, the amplitude A and/or the phase φ of the output signal 32 is measured at the frequency of the input signal 31.

The test base 11 too can, in terms of the invention, take quite many forms. Some examples of these are the so-called lateral-flow test, the pit test, the capillary, the microfluidics channel, the micro array, or some other manner of bringing the particles to be measured into the vicinity of the device 10. For the transportation of larger numbers of particles, it is possible to use the later-flow test, on account of its simplicity, reliability, and inexpensiveness. A particular positioning precision (distance from the coil 13) is expected of smaller amounts of particles and smaller sensor transport formats. Microfluidics is more suitable than the lateral test and a test base 11 that may be integrated permanently in connection with the coil 13 will permit a very high positioning precision relative to the position of the coil 13 and the test base 11 to each other.

The diameter of individual particles, which can be defined using the device 10 according to the invention, can be, for example, in the range 1 nm-10 μm. Of particular interest are the particle clusters, with a diameter that can be, depending on the test base, for example in the range 30 nm-10 μm or particularly 100-600 nm, which are formed, for example, of smaller 5-30-nm particles. The amount of magnetite or a corresponding magnetic material can be, for example, in the order of 1 ng-1 mg and the corresponding sample volume, for example, in the range 1 nl-1 ml. In that case, the number of particles on the test base can be in the range $1-10^{12}$ particles, more particularly in the range $10^3-10^{10}$ (for example, lateral-flow tests) or $1-10^8$ (for example, miniaturized diagnostics). The minimum and maximum of the size and number of the particles generally depends of the application and the dimensions of the coil arrangement used.

The form of the measuring coil 13, as well as that of the other coil devices 18-20 that may belong to the device 10, can be, for example, a polygonal (for example, a square, rectangle, triangle, hexagon), or round (for example, a circle, oval, omega), possibly spiral, planar, continuous, electrically conductive, current-carrying conductor structure.

In the device 10 according to the invention, at least one dimension of the conductor structure in at least one coil structure 13 is in the order of magnitude range of a few micrometers to hundreds of micrometers. Thus, for example, the height i.e. the thickness of the conductor (and at the same time the insulation spacing and winding spacing) can be $10^{-7}-10^{-4}$ m and the width of the conductor $10^{-6}-10^{-4}$ m. Here, the terms heights and thickness of the conductor refer to the direction perpendicular to the base 22 and the term width to the direction parallel to the plane of the base 22.

The scale parallel to the plane (its plane cross-section and/or length and/or width) of each coil 13, 18-20 belonging to the device 10 can be, for example, $10^{-7}-10^{-2}$ m, particularly $10^{-5}-10^{-3}$ m. This is particularly the case in a coil structure formed of several conductors. Depending on the manufacturing technique, the example of the dimensions parallel to the plane can be 3 mm×3 mm or 300 μm×300 μm. Correspondingly, the spacing of the turns of the coils 13, 18-20 can be, for example, 100 μm or 10 μm. In a coil structure applying the bridge construction, the distance of the coils 13, 18-20 from each other can be 1-5 mm, such as, for example 1-3 mm. Thus it is possible to speak generally of macro or micro-coils.

The size of the test base 11 and the reaction area in it depends on the application used and the number of particles. The lateral-flow test, which is suitable for the transportation of larger numbers of particles, can be, for example, 3-mm wide, 50-mm long, and a few hundreds of micrometers thick. The surface area of the test area of a lateral-flow test can be, for example, 3 mm×1 mm, or 5 mm×1 mm. In such a test, the particle distribution can be, for example, relatively homogeneously distribution over the whole thickness of the strip 11. The channel diameter of microfluidics, which is more suitable for the transportation of smaller numbers of particles, can be, for example, about 100 μm and the surface area of the test area, for example, about 300 μm×300 μm. In a test implemented using microfluidics, the particle distribution is in the surface of the test area, for example, or in its immediate vicinity.

The dimensions of the coils 13, 18-20 have a significant effect on the sensitivity of the measuring system. The embodiments shown in FIGS. 1-3 show basic geometries for planar coils. For reasons of simplicity, only rectangular coil forms are shown in this case. Reference has already been made to other possible coil forms. The number of turns, length, thickness, and width of the coils of the embodiments of FIGS. 1-3 can vary relative to each other. The electrical properties of the coils are determined by their geometry and dimensions. Approximate estimates of values, based on the measurements and simulations are given above for the variations (without being restricted to them), for the inductance and resistance, the cross-sectional area of a coil made from copper being about 36 μm×100 μm and the cross-section of the coil being 2-4 mm in the X and Y directions. The impedance determined from these depends on the frequency used.

The following is a brief description of the operating principle of the device 10 according to the invention and of the corresponding method. The magnetic particles 12 can be brought to the measuring area of the measuring coil 13 using a suitable test base 11. The particles reinforce the magnetic field in the environment of the coil 13 when they come under the influence of the magnetic field of the coil 13. The coil 13 experiences this effect as a change in the relative permeability of the environment ($\mu_r>1$). This causes a change (ΔL) in the inductance ($L_0$) of the measuring coil 13.

$$\Delta L = L_0(\mu_r - 1)$$

$$X_L = \omega_0 L_0$$

The change (ΔL) of inductance proportional to the number of particles can be detected as a change in the total impedance (Z) caused by the change ($\Delta X_L$) in the inductive reactance ($X_L$). This improves the performance of the measurement of the amplitude A and/or phase φ at high frequencies. An LC circuit can also be used for the measurement, but in that case, too, the amplitude A (y-axis) and not the frequency is measured.

The inductance (for example, 1-100 nH) of the coil 13 and its change (for example, about 50 fH-50 pH) can be detected by measuring the changes ΔA, Δφ in the amplitude and/or phase of the high-frequency voltage, or current signal 31 fed to the measuring coil 13. The input voltage given by the supply 23 can vary between 0.1-10 V, more particularly between 0.5-2.5 V, and the input current (impedance) between 0.001-10 A, more particularly between 0,05-1 A. The frequency of the input voltage/current can vary between $10^5-10^9$ Hz, more particularly between $10^6-10^8$ Hz (for example, for micro-coils). As an example of the frequency, reference can be made to the use in one macro-scale pilot device of 5-20 MHz, more particularly 7-14 MHz. The measurement of the change ΔA, Δϕ in amplitude and/or phase can be implemented by monitoring the absolute value of the impedance and/or phase ϕ of the measuring coil 13 before and after exposure to the magnetic particles, which monitoring is performed using the frequency of the input signal 31 fed to the coil arrangement 10. The greatest problem in such a measuring arrangement is external interference, which distorts the measurement results and reduces the reliability of the measurement, but its effects can be surprisingly eliminated using the compensating structures 18-20.

A comparison can be implemented, for example, using the differential construction shown in FIGS. 4 and 5, in which the construction is used to compensate the signal from the measured signal caused by the empty measuring coil 13 (impedance of the coil and ambient interference) away at the reference coil 18. Such a differential construction is shown in FIG. 4. In it, two identical spiral coils 13, 18 are connected in series and a high-frequency voltage or current signal 31 is fed over the coils, (typical variation intervals of current, voltage, and frequency above). In an ideal situation, it is possible to assume both coils 13, 18 to be completely identical in inductance and resistance. Thus, the voltage over both coils 13, 18 should sum to zero in the intermediate output 15 between the coils 13, 18. The magnetic particles deviated from this state of balance. The unbalance can be measured, for example as the current/voltage signal 32 of the intermediate output 15.

The sensitivity of the devices 10 shown in FIGS. 4 and 5 can be increased by bringing the coil 13 or the coils 13, 18 into resonance at a suitable frequency (particularly in the range $10^6$-$10^8$ Hz). This can be implemented, for example, using separate LC circuits, by adding suitable capacitors in parallel or in series with the measuring coil/coils of the circuit, as shown in FIG. 6. The value of such a capacitor is determined from, among other things, the inductance of the coil and the desired resonance frequency. For the frequency range referred to, the capacitance can vary (for example, with a 50-nH coil) between 1 fF-1 μF, more particularly 50 pF-500 nF.

The measuring sensitivity can be further improved by using the bridge circuit shown in FIGS. 6-10, in which measurement takes place between the intermediate outputs 15, 17 of two differential structures. The use of this construction will achieve more greater sensitivity and interference tolerance. FIG. 6 shows a general depiction of an impedance bridge, but also other types of bridge solution may be considered. FIG. 6 includes some possible way of placing the resonance capacitors $C_{R1}$-$C_{R6}$. At least some, or even all of these capacitors can be used. The capacitance of the capacitors is determined in a manner that is, as such, known, using the inductance of the coil and the desired resonance frequency as a basis. One example of the capacitance interval can be 1 fF-1 μF, more particularly 50 pF-500 nF.

The signal level of the system can be set to zero by feeding to the output of the system, such as, for example, to the output of the bridge measurement, or the output of the differential measurement, a current and/or voltage signal of the opposite phase and the same amplitude.

Figure 7:
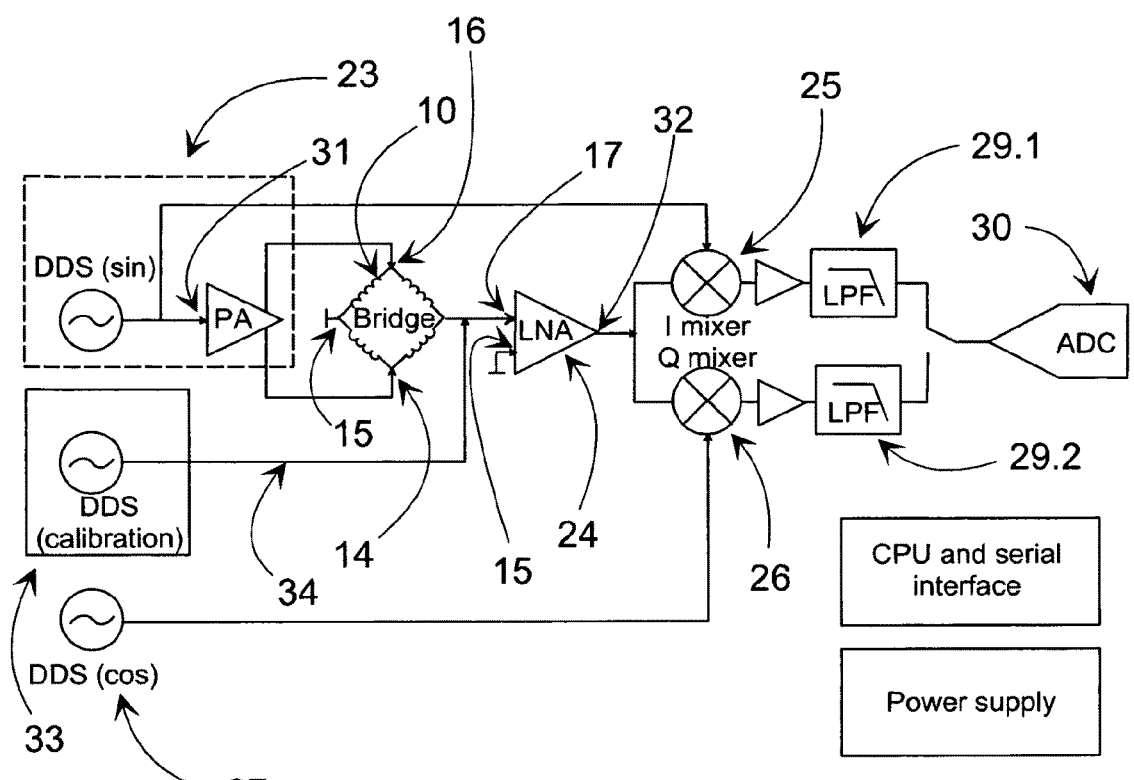

FIG. 7 shows a simplified example of a measuring circuit, which can be applied in the coil arrangement 10 according to FIG. 6. It will be obvious to one skilled in the art, that the measuring arrangement is not intended to restrict the basic idea according to the invention, but is intended only as an example, by means of which measurements according to the invention can be performed.

The first amplifier stage 24 shown in FIGS. 6 and 7 can be, for example, a low-noise (LNA), broadband differential amplifier, such as, for example, the Texas Instruments THS7530. In order to maximize noise immunity, the driving and/or the measuring side of the bridge, i.e. the coil arrangement 10, can be made to float with transformers (not shown). After the amplifier 24, there can be quadrature detection, in order to eliminate low-frequency noise and 50-Hz interference, as well as to permit phase-difference measurements.

The quadrature detection can be implemented using mixers 25, 26 by mixing the output signal 32 with the sine of the input signal 31 formed by the DDS oscillator 23 (Inphase I) and the cosine formed by the DDS oscillator 27 (Quadrature Q).

The outputs of the I and Q mixers 25, 26 are filtered by lowpass filters 29.1, 29.2, amplified, and fed to the 16-bit ADC 30. A third DDS oscillator 33 is arranged to eliminate the difference of the coils 13, 18, 19, 20 belonging to the bridge 10, which appears despite the symmetry and manufacturing precision of the measuring bridge. By means of this feedback, an amplitude and phase-controlled equalization signal 34 is fed to the output of the bridge 10. The signal 34 forces the output of the bridge 10 to zero, when there are no magnetic particles in the sphere of influence of the coil arrangement 10.

In order to reduce the noise level, and prevent feed-through between the modules, the circuit includes the necessary shields and power-supply filters. In addition, each main module can have its own regulator (not shown).

In the concept according to the invention, the output signal 32 should be understood to be the raw signal measured, for example, directly from the bridge 10, or the raw signal, which is manipulated in a manner that is, as such, known, in order to permit measurement. In an ideal case, the raw signal is directly proportional to the number of particles. Due to the non-idealities of the bridge 10, the output signal of the bridge 10 has generally offset. The offset is removed using a calibration signal 34. After this, the amplified signal is the measuring signal 32, directly proportional to the particles, from which measurement can be performed. Other kinds of signal manipulation will also be obvious to one skilled in the art, without, however, altering the basic idea of the invention.

By altering the ratios of the shape and the dimensions (for example, in the plane of the coil) of both the measuring coil 13 and of the reference 18 and/or the compensation coils 19, 20, it is possible to reduce the measuring error caused by errors in the placing of the sample, and thus to increase the robustness of the system.

It should be further noted that the factor that, in the device 10 according to the invention, the reference of the measuring coil 13 comes directly from the adjacent reference coil 18 over a galvanic contact. Through the galvanic contact, the measuring coil 13 and the reference coil 18 can be the same conductor/structure. Even with purely a direct contact between the coils 13, 18, without intermediate electronics will surprisingly eliminate interference. For example, errors due to poor components or asymmetry can be eliminated, if the basic construction is arranged to be as symmetrical and unified as possible.

Figure 11:
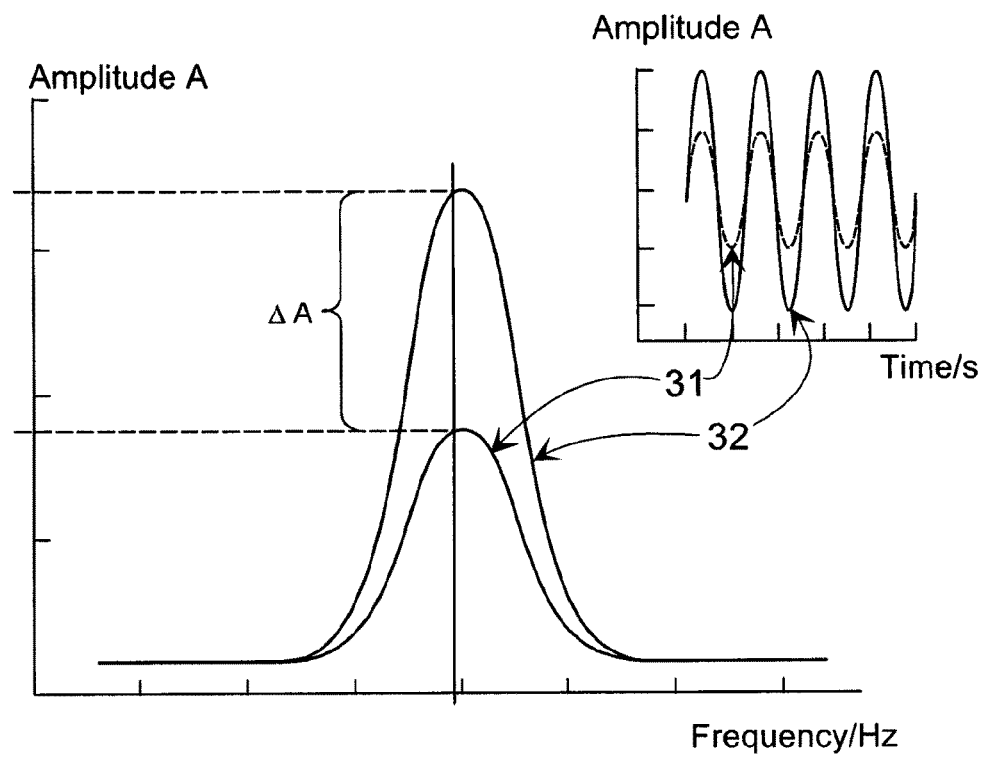
FIG. 11 shows an application example of a graph, in which the change in the inductance of a coil, caused by magnetic particles, is measured as an amplitude measurement.

FIG. 11 shows an example of an application, in which the change in the inductance of the coil arrangement, caused by magnetic particles, is measured as an amplitude measurement. In this case, the amplitude A of the output voltage 32 is measured as a function of the frequency from the intermediate output 15 of the measuring coil 13 and the reference coil 18, in which case the amplitude difference ΔA relative to the input voltage 31 is obtained. The change in inductance, indicated by the amplitude difference ΔA, is converted into an electric signal by feeding a sinusoidal input voltage over the measuring coil 13 and the reference coil 18. The voltage measured from the so-called intermediate output 15 between the coils 13, 18 is determined from the ratio of the impedances (inductances) of the coils 13, 18, and is proportional to the number of magnetic particles. The frequency of the input signal 31, i.e. the frequency at which the output signal 32 is measured, can be, for example, the resonance frequency of the coil system, but the use of other frequencies is also possible.

The insert of FIG. 11 shows the input voltage as a function of time in a situation like that in FIG. 11. It is also possible for changes in the frequency and/or phase of the signal to occur in such measurements. It should be noted that the signal need not be sinusoidal, but that it can also be, for example, a square wave, a triangular wave, a burst, or some other wave shape obvious to one skilled in the art.

Figure 12:
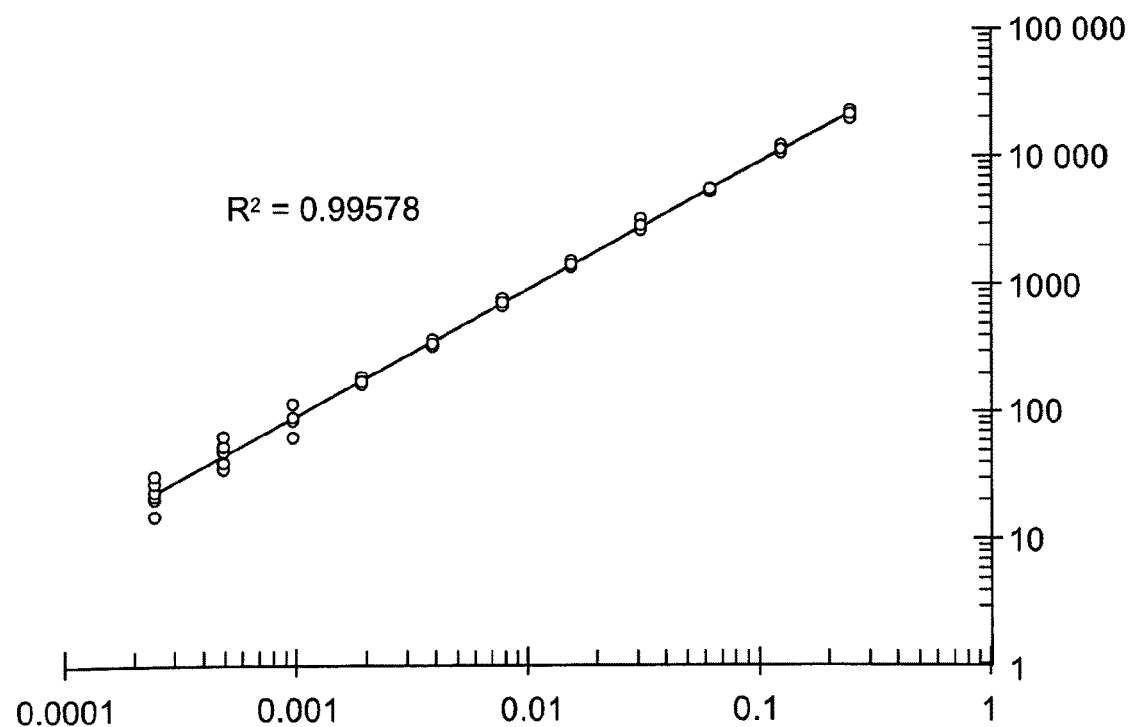
FIG. 12 shows an example of a standard graph obtained using the measuring procedure of FIG. 11.

FIG. 12 shows an example of a typical standard graph obtained using the manner of measuring of FIG. 11. The change $\Delta A$ in amplitude measured is shown on the vertical axis while the relative number of particles is shown on the horizontal axis. The unit of the vertical axis can be, for example, the volt (V), current (I), or even the bit (Bit), when using an AD converter in the signal processing. As can be seen from FIG. 12, the real measurement results follow the great linearity of the logarithmic scale used, the value $R^2$ depicting the deviation of the measurement results from the standard graph is 0.99578.

Figure 13:
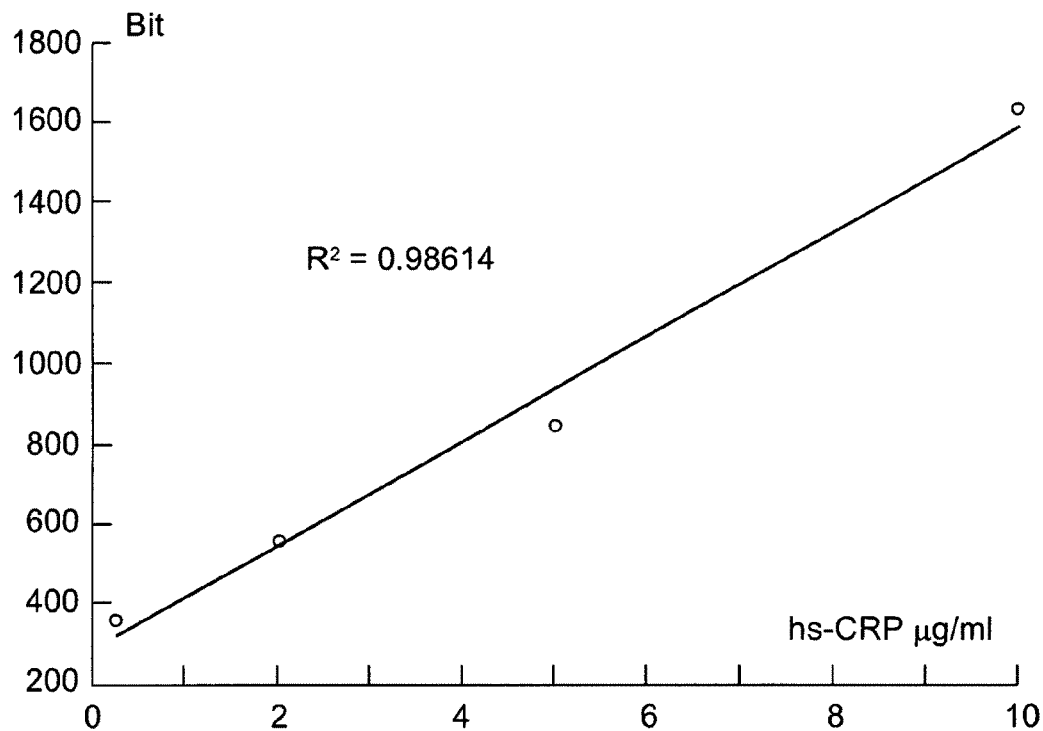
FIG. 13 shows an application example of the measurement of a sample, using the measuring principle according to FIG. 11.

FIG. 13 shows the content CRP (High-sensitivity C-reactive Protein) in a sample, measured using the measuring procedure of FIG. 11. The measured change $\Delta A$ in amplitude is shown on the vertical axis and the CRP content in the sample, proportional to the number of magnetic particles, on the horizontal axis.

Figure 14:
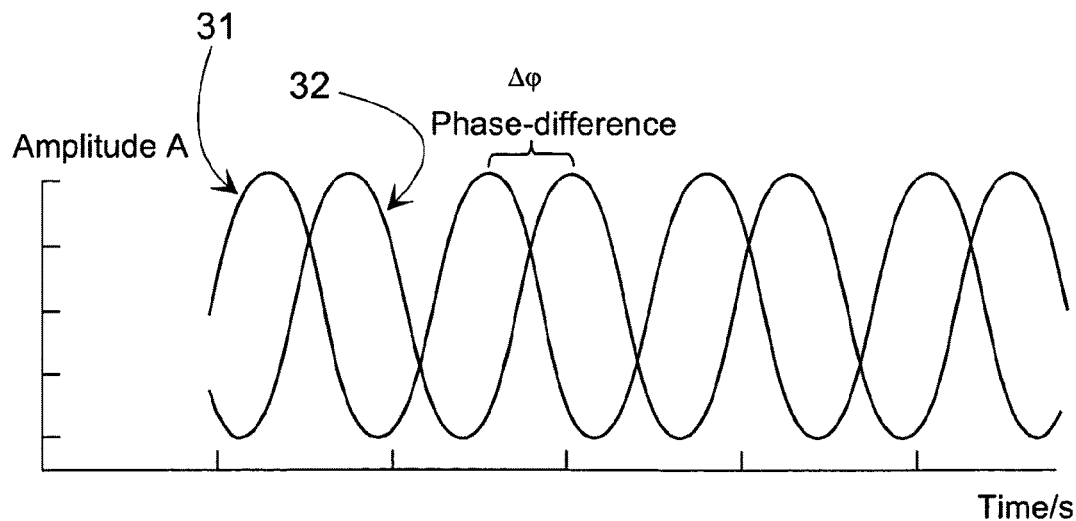
FIG. 14 shows an application example of a graph, in which the change in the inductance of a coil, caused by magnetic particles, is measured as a phase-difference measurement.

FIG. 14 shows an example of an application of a graph, in which, instead of the amplitude A, the phase difference $\Delta\phi$ between the input voltage 31 and the output voltage 32 is measured. In this case too, the measurement was performed from (intermediate output 15) between the measuring coil 13 and the reference coil 18. In this case too, it is also possible for changes in the frequency and/or the amplitude to occur in the measurement. Instead of being sinusoidal, the signal can also be, for example, a square wave, triangular wave, burst, or some other signal shape obvious to one skilled in the art.

In the device 10 according to the invention, it is possible to use almost ideal reference signals, which measure out the background (unspecifically bound magnetic particles) from the sample and remove, in addition, external interferences (for example the Earth's magnetic field).

It must be understood that the above description and the related figures are only intended to illustrate the present invention. The invention is thus in no way restricted to only the embodiments disclosed or stated in the Claims, but many different variations and adaptations of the invention, which are possible within the scope on the inventive idea defined in the accompanying Claims, will be obvious to one skilled in the art.

The invention claimed is:

1. Device for the qualitative or quantitative measurement of a magnetically labelled analyte, which device includes a coil arrangement, formed of at least one measuring coil and a reference coil arranged in connection with it, for measuring the analyte from a sample absorbed in a test base, and from the intermediate output signal of which coil arrangement a change in inductance correlating to the content of the magnetically labelled analyte is arranged to be detected, characterized in that the said change in inductance is arranged to be detected from a change ($\Delta A$, $\Delta\phi$) in amplitude and/or phase appearing in the output signal measured from the intermediate output of the coil arrangement, which is arranged to be measured at the frequency of the input signal and the device includes in addition a coil arrangement compensating error signals, for example, for compensating error signals caused by the environment and/or magnetic particles bound unspecifically to the test base.

2. Device according to claim 1, characterized in that, in order to increase the inductive reactance of the measuring coil to be greater than the resistance, the measuring frequency of the device is arranged to be $10^6$-$10^8$ Hz.

3. Device according to claim 1, characterized in that at least the reference coil is an identical copy or mirror image of the measuring coil.

4. Device according to claim 1, characterized in that the measuring coil, the reference coil, and the possible compensating coil structure is arranged to form a differential coil arrangement.

5. Device according to claim 1, characterized in that the compensating coil structure includes at least two coils, which are arranged symmetrically relative to the measuring coil and the reference coil.

6. Device according to claim 1, characterized in that the measuring coil, the reference coil, and the compensating coil structure are arranged relative to each other in an impedance bridge.

7. Device according to claim 1, characterized in that the measuring coil, the reference coil, and the compensating coil structure are of the same magnitude in the case of at least one electrical parameter.

8. Device according to claim 6, characterized in that the coils forming the impedance bridge are in a planar matrix formation.

9. Device according to claim 6, characterized in that the coils forming the impedance bridge are in a layered formation.

10. Device according to claim 1, characterized in that the test base is integrated with the device, in such a way that it interactively in connection with the coil arrangement.

11. Device according to claim 1, characterized in that the scale of the coils in the plane direction is $10^{-7}$-$10^{-2}$ m.

12. Device according to claim 1, characterized in that the coils are arranged to form a conductor structure, in which the thickness of the conductor is $10^{-7}$-$10^{-4}$ m and the width $10^{-6}$-$10^{-4}$ m.

13. Device according to claim 1, characterized in that the measuring coil and the reference coil are aligned symmetrically relative to the measuring-signal conductors.

14. Method for the qualitative or quantitative measurement of an analyte, in which a test base is used to measure the analyte, and in which method
a sample is absorbed into the test base, and
the test base is analysed using a coil arrangement, from the signal of which intermediate output a change in inductance correlating to the content of the magnetically labelled analyte is detected,
characterized in that the change in inductance is detected from a change ($\Delta A$, $\Delta\phi$) in amplitude and/or phase appearing in the output signal of the intermediate output of the coil arrangement, which is measured at the frequency of the input signal and, in addition, error signals caused by the environment and/or magnetic particles bound unspecifically to the test base are compensated by a coil arrangement.

15. Method according to claim 14, characterized in that the coil arrangement includes at least one measuring coil and a reference coil arranged in connection, with it, and in order to increase the inductive reactance of the measuring coil to be greater than the resistance, the measurement is performed using a measuring frequency of $10^6$-$10^8$ Hz.

16. Method according to claim 15, characterized in that the compensation is performed using a differential coil arrangement.

17. Method according to any of claim 14, characterized in that in the method the sample is absorbed to a test base, which is integrated interactively with at least part of the coil arrangement.

18. Device according to claim 1 characterized in that the scale of the coils in the plane direction is $10^{-5}$-$10^{-3}$ m.

* * * * *